(12) United States Patent
Retsina et al.

(10) Patent No.: US 9,487,840 B2
(45) Date of Patent: Nov. 8, 2016

(54) PROCESSES AND APPARATUS FOR REFINING SUGARCANE TO PRODUCE SUGARS, BIOFUELS, AND/OR BIOCHEMICALS

(71) Applicant: API Intellectual Property Holdings, LLC, Atlanta, GA (US)

(72) Inventors: Theodora Retsina, Atlanta, GA (US); Ryan O'Connor, Minnetrista, MN (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 72 days.

(21) Appl. No.: 14/487,070

(22) Filed: Sep. 15, 2014

(65) Prior Publication Data

US 2015/0079639 A1 Mar. 19, 2015

Related U.S. Application Data

(60) Provisional application No. 61/878,421, filed on Sep. 16, 2013.

(51) Int. Cl.
| | |
|---|---|
| F23G 7/10 | (2006.01) |
| C13B 20/00 | (2011.01) |
| C12P 7/06 | (2006.01) |
| C12P 19/02 | (2006.01) |
| C13B 35/08 | (2011.01) |
| C12P 19/14 | (2006.01) |
| C13K 13/00 | (2006.01) |
| C13K 1/02 | (2006.01) |

(52) U.S. Cl.
CPC .............. *C13K 13/00* (2013.01); *C12P 7/06* (2013.01); *C12P 19/02* (2013.01); *C12P 19/14* (2013.01); *C13B 20/002* (2013.01); *C13B 35/08* (2013.01); *C13K 1/02* (2013.01); *F23G 7/10* (2013.01); *C12P 2201/00* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 2007/0298477 A1* | 12/2007 | Kratochvil | C12P 7/10 435/165 |
| 2008/0057555 A1* | 3/2008 | Nguyen | C12P 7/10 435/165 |

(Continued)

FOREIGN PATENT DOCUMENTS

| | | | | |
|---|---|---|---|---|
| WO | WO 01/14594 | * | 3/2001 | |
| WO | WO 2012/001688 | * | 1/2012 | G01N 33/00 |

*Primary Examiner* — Karen Cochrane Carlson
*Assistant Examiner* — Jennifer M. H. Tichy
(74) *Attorney, Agent, or Firm* — Ryan P. O'Connor

(57) ABSTRACT

Conventionally, sugarcane processing avoids leaving residual sucrose in the bagasse, since the bagasse will be burned and the value of the sucrose would be lost. However, when coupled with a Green Power+® process to extract hemicelluloses, sucrose may also be extracted and recovered from the bagasse. In some variations, a process includes mechanically treating a feedstock to generate a sucrose-rich stream and lignocellulosic material that intentionally retains a significant amount of the initial sucrose in the feedstock; extracting the lignocellulosic material with steam and/or hot water to produce cellulose-rich solids and an extract liquor containing hemicellulosic oligomers and sucrose; and then hydrolyzing the hemicellulosic oligomers into a hemicellulose sugar stream. Each of the sucrose-rich stream and the hemicellulose sugar stream (containing the starting residual sucrose) may be recovered or further processed (e.g., fermented to ethanol). Similar processes are possible with energy cane, sugar beets, and energy beets.

20 Claims, 1 Drawing Sheet

(56) References Cited

U.S. PATENT DOCUMENTS

2011/0053238 A1* 3/2011 Ohgren Gredegard ... C12P 7/06
　　　　　　　　　　　　　　　　　　　　　　　435/165

2011/0097777 A1* 4/2011 Oliveira .................... C13B 5/02
　　　　　　　　　　　　　　　　　　　　　　　435/161
2012/0009632 A1* 1/2012 Retsina ............... C08B 37/0003
　　　　　　　　　　　　　　　　　　　　　　　435/105

* cited by examiner

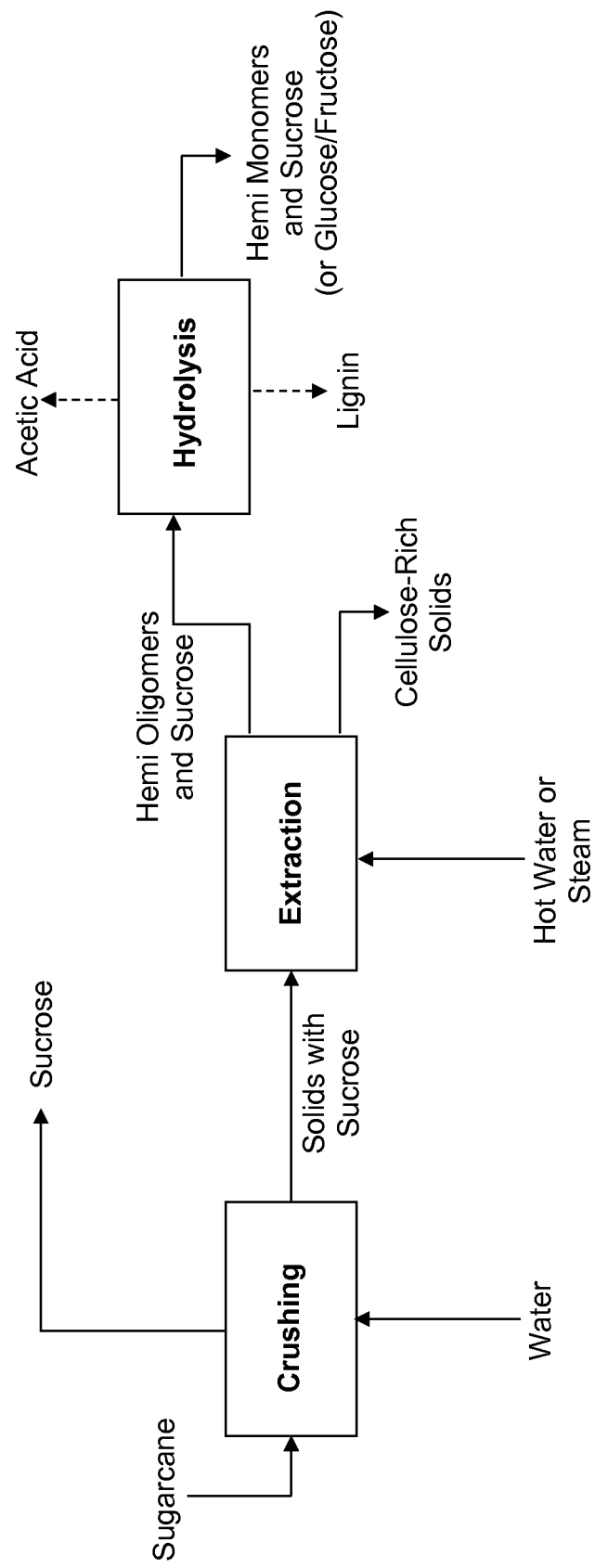

PROCESSES AND APPARATUS FOR REFINING SUGARCANE TO PRODUCE SUGARS, BIOFUELS, AND/OR BIOCHEMICALS

PRIORITY DATA

This patent application is a non-provisional application with priority to U.S. Provisional Patent App. No. 61/878,421 filed Sep. 16, 2013, which is hereby incorporated by reference herein in its entirety.

FIELD OF THE INVENTION

The present invention generally relates to processes for refining sugarcane and related feedstocks to produce sugars, including sucrose and hemicellulose sugars, which are optionally purified, fermented to biofuels or biochemicals, or recovered for other uses.

BACKGROUND OF THE INVENTION

Sugarcane is the world's largest crop. Brazil is the largest producer of sugarcane in the world. The world demand for sugar is the primary driver of sugarcane agriculture. Sugarcane accounts for about 80% of sugar produced; most of the rest is made from sugar beets. Sugarcane predominantly grows in the tropical and subtropical regions, and sugar beet predominantly grows in colder temperate regions of the world.

The production of sugar (sucrose) from raw sugarcane is well-known. Furthermore, the development of equipment and associated processes for producing sugar from sugarcane stalks has been extensive. Generally, sugar product is produced from a naturally occurring liquid contained within the cells of sugarcane stalks.

In particular, the recovery of sucrose from the cane plant requires the separation of juice from the fibrous material in the structure of the stalk. The tissue inside the rind of the stalk is a matrix of thin-walled parenchyma cells in which are imbedded vascular bundles. Sucrose is present principally in the parenchyma storage cells. These cells are easily ruptured and the most commonly employed methods to extract the juice are by milling or crushing, hot-water extraction, or a combination of these methods. In the hot-water extraction method, cane is typically prepared by knife mills and roller-crusher combinations.

Recently, the Green Power+® technology has been developed by American Process, Inc. based in Atlanta, Ga., United States. Green Power+ technology is capable of extracting hemicellulose sugars and acetic acid from lignocellulosic biomass, including sugarcane bagasse, sugarcane straw, and related feedstocks. In the Green Power+ process, the hemicelluloses are extracted using steam or liquid hot water and then converted to monomer sugars using a catalyst (acids or enzymes). The acetic acid can be recovered in the form of acetic acid or acetate.

Most sugarcane ethanol mills are in remote locations and use the bagasse to generate the necessary steam and power to run the mill and occasionally export to the local grid. It is therefore not viable to divert all the bagasse to the production of cellulosic ethanol. However, the diversion of only the hemicelluloses of the bagasse to the production of cellulosic ethanol is robust and financially attractive proposition, leading to competitive production of cellulosic ethanol. Such an application using the Green Power+ technology can result in incremental cellulosic ethanol production in an existing sugarcane ethanol mill and still allow the mill to produce its steam and power energy needs (possibly an energy surplus).

Further improvements in sugarcane processing are desired. It would be desirable to utilize Green Power+ technology so that hemicellulose sugars and other co-products may be economically obtainable, along with sucrose or fermentation products from the sucrose.

SUMMARY OF THE INVENTION

The present invention addresses the aforementioned needs in the art.

In some variations, the invention provides a process for refining a sucrose-containing feedstock, the process comprising:

(a) providing a feedstock containing lignocellulosic material and sucrose;

(b) mechanically treating the feedstock to generate a sucrose-rich stream and sucrose-depleted lignocellulosic material, wherein the sucrose-depleted lignocellulosic material retains at least 1% of the initial sucrose contained in the feedstock;

(c) extracting the sucrose-depleted lignocellulosic material with steam and/or hot water to produce cellulose-rich solids and an extract liquor containing hemicellulosic oligomers and extracted sucrose;

(d) hydrolyzing the hemicellulosic oligomers into a hemicellulose sugar stream, wherein the hemicellulose sugar stream comprises the extracted sucrose or a hydrolyzed form thereof (e.g., glucose and fructose);

(e) recovering or further processing the hemicellulose sugar stream;

(f) recovering or further processing the sucrose-rich stream; and (g) combusting the cellulose-rich solids to produce steam and/or electricity.

In some embodiments, the feedstock is selected from the group consisting of sugarcane, energy cane, sugar beets, and energy beets. In certain embodiments, the feedstock is sugarcane and the lignocellulosic material contains sugarcane bagasse and optionally sugarcane straw.

Some amount of sucrose is intentionally left in the lignocellulosic material. The extracted lignocellulosic material retains at least 2%, 3%, 4%, 5%, or more of the initial sucrose contained in the feedstock, in various embodiments. In some embodiments, the extracted lignocellulosic material retains from about 1% to about 10% of the initial sucrose contained in the feedstock, such as about 2% to about 7% or about 3% to about 6% of the initial sucrose contained in the feedstock.

Optionally, step (c) further includes introducing an extraction catalyst. The extraction catalyst may be an organic acid (such as acetic acid), an inorganic acid (such as sulfuric acid or sulfurous acid), or a combination thereof.

In some embodiments, step (d) employs an acid catalyst for hydrolyzing the hemicellulosic oligomers. In other embodiments, step (d) employs an enzyme catalyst for hydrolyzing the hemicellulosic oligomers.

At least a portion of the hemicellulose sugar stream may be fermented to a fermentation product. In these or other embodiments, at least a portion of the hemicellulose sugar stream may be recovered as purified hemicellulose sugars.

At least a portion of the sucrose-rich stream may be fermented to ethanol or another fermentation product. In these or other embodiments, at least a portion of the sucrose-rich stream may be recovered as purified sucrose sugar. In a certain embodiment, the sucrose is purified and sold as a sugar product while the hemicellulose sugars are fermented to cellulosic ethanol or another fermentation product.

In some embodiments, the process further comprises recovering lignin derived from the sucrose-depleted lignocellulosic material. The lignin may be recovered from the extract liquor during or after step (c), during or after hydrolysis of hemicellulosic oligomers in step (d), or during or after step (e). The recovered lignin may be combusted, optionally in combination with the cellulose-rich solids combusted in step (g).

Certain variations relating specifically to sugarcane refining comprise the steps of:

(a) providing a feedstock containing sugarcane;

(b) mechanically treating the feedstock to generate a sucrose-rich stream and sucrose-depleted lignocellulosic material, wherein the sucrose-depleted lignocellulosic material retains from about 1% to about 10% of the initial sucrose contained in the sugarcane;

(c) extracting the sucrose-depleted lignocellulosic material with steam and/or hot water to produce cellulose-rich solids and an extract liquor containing hemicellulosic oligomers and extracted sucrose;

(d) hydrolyzing the hemicellulosic oligomers into a hemicellulose sugar stream, wherein the hemicellulose sugar stream comprises the extracted sucrose or a hydrolyzed form thereof;

(e) recovering or further processing the hemicellulose sugar stream;

(f) recovering or fermenting the sucrose-rich stream; and (g) combusting the cellulose-rich solids to produce steam and/or electricity.

The present invention provides a process for refining a sucrose-containing feedstock, the process comprising:

(a) providing a feedstock containing lignocellulosic material and sucrose;

(b) mechanically treating the feedstock to generate a sucrose-rich stream and sucrose-depleted lignocellulosic material, wherein the extracted lignocellulosic material retains at least 1% of the initial sucrose contained in the feedstock;

(c) extracting the sucrose-depleted lignocellulosic material with steam and/or hot water to produce cellulose-rich solids and an extract liquor containing hemicellulosic oligomers;

(d) hydrolyzing the hemicellulosic oligomers into a hemicellulose sugar stream;

(e) recovering or further processing the hemicellulose sugar stream; and (f) recovering or further processing the sucrose-rich stream.

In some embodiments, the cellulose-rich solids are combusted to produce steam and/or electricity. In some embodiments, the cellulose-rich solids are pelletized. In certain embodiments, the cellulose-rich solids are utilized as a pulp product or pulp intermediate. In any of these or other embodiments, the cellulose-rich solids are hydrolyzed with enzymes or chemical catalysts to produce glucose.

BRIEF DESCRIPTION OF THE FIGURE

FIG. 1 is a simplified block-flow diagram depicting the process of some embodiments of the present invention. Dashed lines indicate optional streams.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

Some variations of the present invention are premised on the realization that certain advantages may arise when sugarcane is less ground, in a manner that retains (for example) the last 1-5% of the initial sucrose in the bagasse. Conventionally, sugarcane processing avoids leaving residual sucrose in the bagasse, since the bagasse will be burned and sucrose combustion destroys the value as sugar. However, when coupled with a Green Power+ process to pre-extract hemicelluloses, it has been recognized that sucrose will also be extracted into solution and may then be obtained as part of the Green Power+ application. Similar processes are possible with energy cane, sugar beets, energy beets, and related feedstocks. This process is contrary to the prior art which teaches that sucrose should not remain in the bagasse or other residual material.

FIG. 1 is a simplified block-flow diagram depicting the process of some embodiments pertaining to sugarcane. Similar processes may be configured for other sucrose-containing feedstocks. In FIG. 1, the unit operation labeled "Crushing" is for mechanically treating the sugarcane to generate a sucrose-rich stream (labeled "Sucrose") and sucrose-depleted lignocellulosic material (labeled "Solids with Sucrose"), wherein the sucrose-depleted lignocellulosic material preferably retains at least 1% of the initial sucrose contained in the sugarcane. The "Extraction" unit operation is for extracting the sucrose-depleted lignocellulosic material with steam and/or hot water to produce cellulose-rich solids and an extract liquor (labeled "Hemi Oligomers and Sucrose") containing hemicellulosic oligomers and extracted sucrose. The "Hydrolysis" unit operation is for hydrolyzing the hemicellulosic oligomers into a hemicellulose sugar stream (labeled "Hemi Monomers and Sucrose (or Glucose/Fructose)" in FIG. 1). Acetic acid and lignin may also be recovered, in some embodiments.

In some variations, the invention provides a process for refining a sucrose-containing feedstock, the process comprising:

(a) providing a feedstock containing lignocellulosic material and sucrose;

(b) mechanically treating the feedstock to generate a sucrose-rich stream and sucrose-depleted lignocellulosic material, wherein the sucrose-depleted lignocellulosic material retains at least 1% of the initial sucrose contained in the feedstock;

(c) extracting the sucrose-depleted lignocellulosic material with steam and/or hot water to produce cellulose-rich solids and an extract liquor containing hemicellulosic oligomers and extracted sucrose;

(d) hydrolyzing the hemicellulosic oligomers into a hemicellulose sugar stream, wherein the hemicellulose sugar stream comprises the extracted sucrose or a hydrolyzed form thereof;

(e) recovering or further processing the hemicellulose sugar stream;

(f) recovering or further processing the sucrose-rich stream; and (g) optionally combusting the cellulose-rich solids to produce steam and/or electricity.

In some embodiments, the feedstock is selected from the group consisting of sugarcane, energy cane, sugar beets, and energy beets. In certain embodiments, the feedstock is sugarcane and the lignocellulosic material is or contains sugarcane bagasse and/or sugarcane straw. Bagasse may be combined with sugarcane straw (also known as trash), following step (b). The sugarcane straw may be subjected to extraction with steam and/or hot water to produce cellulose-rich solids and an extract liquor containing hemicellulosic oligomers. This step could be done in isolation from the extraction of bagasse (containing residual sucrose) or it could be done in combination, where the bagasse and straw are co-fed to step (c) above.

In some embodiments, the bagasse and straw are not separated in the first place. In many sugar mills around the world, burning the standing sugarcane to facilitate cutting and lifting for transport to the mill is common practice. When standing sugarcane is not burned, all of the lignocellulosic material may be processed by the methods disclosed herein.

Some amount of sucrose is intentionally left in the lignocellulosic material. The extracted lignocellulosic material retains at least 1%, 2%, 3%, 4%, 5% (by mass), or more of the initial sucrose contained in the feedstock, in various embodiments. In some embodiments, the extracted lignocellulosic material retains from about 1% to about 10% of the initial sucrose contained in the feedstock, such as about 2% to about 7% or about 3% to about 6% of the initial sucrose contained in the feedstock. In some embodiments, the extracted lignocellulosic material retains more than about 10%, such as about 20%, 30%, 40%, 50% or more (but less than all) of the initial sucrose contained in the feedstock.

In some embodiments, conventional processing (prior art) tends to leave a certain residual amount of sucrose in the lignocellulosic material, such as about 0.1 wt %, 0.2 wt %, 0.3 wt %, 0.4 wt %, 0.5 wt %, 0.6 wt %, 0.7 wt %, 0.8 wt %, 0.9 wt %, or 1 wt % sucrose. In the process of the invention, chemical and/or physical process conditions are adjusted so that the residual amount of sucrose is higher than the conventional amount.

Mechanically treating the feedstock to generate a sucrose-rich stream and sucrose-depleted lignocellulosic material is well-known in the art of sugarcane processing. See, for example, Chen and Chou, *Cane Sugar Handbook*, Twelfth Edition, John Wiley and Sons, Inc., NY, 1993. Mechanical treatment here is for the extraction of cane juice, not the initial mechanical harvesting of sugarcane (e.g., cutting and lifting)—although in principle there could be extraction of cane juice during initial mechanical harvesting.

In some embodiments, the cut sugarcane stalks are initially transferred onto a conveyer table where they are subjected to a standard washing step to reduce impurities on the surface of the stalks. Subsequently, the sugarcane stalks may be conveyed through a standard crushing or chopping apparatus to reduce the stalks into smaller individual pieces for feeding through a series of roller mills, as is well-known to those skilled in the art. In the present invention, the conditions of the crushing or chopping (or other mechanical treatment) are adjusted, controlled, or optimized so that a selected quantity of sucrose is retained in the bagasse.

It may be preferable to limit the hydraulic pressure during crushing or chopping so that some sucrose is retained in the bagasse. The limited hydraulic pressure may also minimize the undesirable extraction of natural waxes, ferrous compounds, and other minerals from the cortex of the sugarcane. For example, the instantaneous hydraulic pressure or the average hydraulic pressure may be controlled to be less than 19 MPa (megapascal), 18 MPa, 17 MPa, 16 MPa, 15 MPa, 14 MPa, 13 MPa, 12 MPa, 11 MPa, 10 MPa, 9 MPa, 8 MPa, 7 MPa, 6 MPa, 5 MPa, 4 MPa, 3 MPa, 2 MPa, or 1 MPa.

In some embodiments, hot-water maceration may aid in the extraction of sucrose. Hot water tends to dissolve natural waxes and minerals in the hard, outer cortex of the cane stalk. It may be desirable to limit the temperature of hot-water maceration so that some sucrose is retained in the bagasse. For example, the instantaneous or average maceration temperature may be controlled to be less than 100° C., 90° C., 80° C., 70° C., 60° C., 50° C., 40° C., or 30° C. In some embodiments, cold-water maceration (e.g., at 20-30° C.) may be utilized.

It may be desirable to limit the residence time of hot-water maceration so that some sucrose is retained in the bagasse. For example, the instantaneous or average maceration residence time may controlled to be less than 60, 55, 50, 45, 40, 35, 30, 25, 20, 15, 10, or 5 minutes. Generally, lower residence times will require higher maceration temperatures.

In some variations, Green Power+® technology, commonly owned with this patent application, may be employed or modified for steps (c)-(e). Green Power+ technology is taught in patents and patent applications commonly assigned with this patent application. Some embodiments employ conditions described in U.S. Pat. Nos. 8,211,680, 8,518,213, 8,518,672, 8,679,364, 8,685,685, or 8,785,155. Each of these commonly owned patents is hereby incorporated by reference herein in its entirety.

Optionally, step (c) further includes introducing an extraction catalyst. The extraction catalyst may be an organic acid (such as acetic acid), an inorganic acid (such as sulfuric acid or sulfurous acid), or a combination thereof.

In some embodiments, step (d) employs an acid catalyst for hydrolyzing the hemicellulosic oligomers. In other embodiments, step (d) employs an enzyme catalyst for hydrolyzing the hemicellulosic oligomers.

At least a portion of the hemicellulose sugar stream may be fermented to a fermentation product. In these or other embodiments, at least a portion of the hemicellulose sugar stream may be recovered as purified hemicellulose sugars.

At least a portion of the sucrose-rich stream may be fermented to ethanol or another fermentation product. In these or other embodiments, at least a portion of the sucrose-rich stream may be recovered as purified sucrose sugar. In a certain embodiment, the sucrose is purified and sold as a sugar product while the hemicellulose sugars are fermented to cellulosic ethanol or another fermentation product.

In some embodiments, the process further comprises recovering lignin derived from the sucrose-depleted lignocellulosic material. The lignin may be recovered from the extract liquor during or after step (c), during or after hydrolysis of hemicellulosic oligomers in step (d), or during or after step (e). The recovered lignin may be combusted, optionally in combination with the cellulose-rich solids combusted in step (g).

In some embodiments, the sucrose-depleted lignocellulosic material is fed to a pressurized extraction vessel operating continuously or in batch mode. The sucrose-depleted lignocellulosic material may be steamed or water-washed to remove dirt and entrained air. The sucrose-depleted lignocellulosic material may be immersed with aqueous liquor or saturated vapor and heated to a temperature between about 100° C. to about 250° C., for example 150° C., 160° C., 170° C., 180° C., 190° C., 200° C., or 210° C. Preferably, the sucrose-depleted lignocellulosic material is heated to about 180° C. to 210° C. The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The extraction liquor (steam or hot water) may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

The process may include depressurization of the cellulose-rich solids. The vapor can be used for heating the incoming feedstock or extraction liquor, directly or indirectly. The volatilized organic acids (e.g., acetic acid) which are generated may be recycled.

The process may include washing the cellulose-rich solids. The washing may be accomplished with water, recycled condensates, recycled permeate, or combinations thereof. A countercurrent configuration may be used to maximize the biomass extract concentration. Washing typically removes most of the dissolved material, including hemicelluloses and minerals. The final consistency of the dewatered cellulose-rich solids may be increased to 30% or more, preferably to 50% or more, using a mechanical pressing device.

The process may include drying of the cellulose-rich solids to a desired final moisture. The heat necessary for drying may be derived from combusting part of the starting biomass. Alternatively, or additionally, the heat for drying may be provided by other means, such as a natural gas boiler or other auxiliary fossil fuel, or from a waste heat source.

The process may include treatment of the extract liquor containing hemicellulosic oligomers to form a hydrolysate comprising fermentable hemicellulose sugars. In some embodiments, the biomass extract is hydrolyzed using dilute acidic conditions at temperatures between about 100° C. and 190° C., for example about 120° C., 130° C., 140° C., 150° C., 160° C., or 170° C., and preferably from 120° C. to 150° C. The sucrose may be hydrolyzed to glucose and fructose, at least to some extent.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis. Alternatively, hemicellulase enzymes may be used instead of acid hydrolysis. The lignin from this step may be separated and recovered, or sent directly to the boiler.

The process may include evaporation of hydrolysate to remove some or most of the volatile acids. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. The dissolved solids are concentrated, such as to about 10% to about 40% to optimize fermentable hemicellulose sugar concentration to a particular microorganism.

In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to assist in the removal of minerals from the biomass. This recycle of organic acids, such as acetic acid, may be optimized along with process conditions that may vary depending on the amount recycled, to improve the cooking and/or washing effectiveness.

In some embodiments, the fermentable hemicellulose sugars are recovered from solution, in purified form. In some embodiments, the fermentable hemicellulose sugars are fermented to produce of biochemicals or biofuels such as (but by no means limited to) ethanol, 1-butanol, isobutanol, acetic acid, lactic acid, succinic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled. Use of the fermentation residual solids may require further removal of minerals. Generally, any leftover solids may be used for burning as additional liquefied biomass, after concentration of the distillation bottoms.

Part or all of the residual solids may be co-combusted, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

Optionally, the process may include co-combusting the recovered lignin to produce power. The recovered lignin may be combined with the energy-dense biomass prior to combustion, or they may be co-fired as separate streams. When recovered lignin is combined with the energy-dense biomass for making pellets, the lignin can act as a pellet binder.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate, such as through electrolytic reduction to acetic acid.

Certain variations relating specifically to sugarcane refining comprise the steps of:

(a) providing a feedstock containing sugarcane;

(b) mechanically treating the feedstock to generate a sucrose-rich stream and sucrose-depleted lignocellulosic material, wherein the sucrose-depleted lignocellulosic material retains from about 1% to about 10% of the initial sucrose contained in the sugarcane;

(c) extracting the sucrose-depleted lignocellulosic material with steam and/or hot water to produce cellulose-rich solids and an extract liquor containing hemicellulosic oligomers and extracted sucrose;

(d) hydrolyzing the hemicellulosic oligomers into a hemicellulose sugar stream, wherein the hemicellulose sugar stream comprises the extracted sucrose or a hydrolyzed form thereof (i.e., glucose plus fructose);

(e) recovering or further processing the hemicellulose sugar stream;

(f) recovering or fermenting the sucrose-rich stream; and (g) combusting the cellulose-rich solids to produce steam and/or electricity.

There are many options that may be employed regarding sugar recovery or further processing. In some embodiments, the sucrose-rich stream is recovered and purified as a sugar product in dry form or as a syrup, for example. The sucrose that is diverted to the hemicellulose sugar stream, according to the processes disclosed, may be recovered in principle but typically will be converted by fermentation into a product such as ethanol.

It is possible to convert the main sucrose fraction into a product, such as a biochemical (e.g., lactic acid) while the hemicellulose sugars are converted to a different product, such as a biofuel (e.g., ethanol). It is also possible to recombine some or all of the sugars, if desired, for common fermentation or other processing.

In addition, all of these options are dynamic. A plant may operate to maximize pure sugar for some period of time and then, depending on economic conditions, time of year, weather factors, or policy changes, shift to production of biofuels/biochemicals from the sucrose. Along with these dynamic adjustments in operation, the amount of residual sucrose remaining in the bagasse according to the disclosed process may vary, to shift the product portfolio. For example if the balance will shift from sugars toward biofuels/biochemicals, it may be beneficial to allow more sucrose to remain in the bagasse to take advantage of fermentation capacity, etc.

The sucrose may survive step (d) above or may be converted to glucose and fructose, depending on conditions. It may be desirable for some or all of the sucrose to hydrolyze to glucose and fructose. In other embodiments, it may be desirable for most or all of the sucrose to be preserved as sucrose (a $C_{12}$ sugar).

The present invention provides a process for refining a sucrose-containing feedstock, the process comprising:

(a) providing a feedstock containing lignocellulosic material and sucrose;

(b) mechanically treating the feedstock to generate a sucrose-rich stream and sucrose-depleted lignocellulosic material, wherein the extracted lignocellulosic material retains at least 1% of the initial sucrose contained in the feedstock;

(c) extracting the sucrose-depleted lignocellulosic material with steam and/or hot water to produce cellulose-rich solids and an extract liquor containing hemicellulosic oligomers and extracted sucrose;

(d) hydrolyzing the hemicellulosic oligomers into a hemicellulose sugar stream, wherein the hemicellulose sugar stream comprises the extracted sucrose or a hydrolyzed form thereof;

(e) recovering or further processing the hemicellulose sugar stream; and (f) recovering or further processing the sucrose-rich stream.

In some embodiments, the cellulose-rich solids are combusted to produce steam and/or electricity. In some embodiments, the cellulose-rich solids are pelletized. In certain embodiments, the cellulose-rich solids are utilized as a pulp product or pulp intermediate (i.e., an intermediate material that may be further refined, bleached, or otherwise treated). In any of these or other embodiments, the cellulose-rich solids are hydrolyzed to produce glucose.

As mentioned previously, this invention is by no means limited to sugarcane processing. The principles described herein may be applied by one skilled in the art to energy cane, sugar beets, energy beets, and any other crops or biomass containing sucrose.

When applied to sugar beets, the Green Power+ process may be employed for sugar beet pulp, sugar beet tailings, or both of these, for example. At a processing plant, foreign material, small beets (such as broken beets), and leaves are removed from the beets prior to processing. This material is known as "sugar beet tailings." Sugar beet tailings may be subjected to steam or hot-water extraction to remove sugars, and there will typically be some sucrose as well, due to small beets present in the tailings.

Following removal of the tailings, the sugar beets are sliced into long strips called cossettes. The cossettes are cooked in hot water to remove the sugar. Then the hot water and sugar mixture is further processed into bulk or bagged sugar, or further treated (e.g., fermented). The residual solids following removal of sugar is sugar beet pulp. The temperature and/or residence time of the hot-water cooking may be controlled, as explained above with respect to sugarcane, to leave some amount of sucrose behind.

In some embodiments relating to sugar beets, no initial removal of sugar beet tailings is performed. Rather, all of the sugar beet feedstock may be subjected to a hot-water extraction to remove sucrose, and the remaining material may then be processed by Green Power+ technology to recover other sugars (e.g., hemicelluloses).

The present invention also includes apparatus configured to carry out any of the disclosed processes. In general, one of ordinary skill in the art will understand that known equipment is commercially available and may be configured to carry out these processes. Reference is also made to the Green Power+ patents and patent applications that have been incorporated by reference herein.

The present invention also includes compositions, products, and intermediates that are produced by any of the disclosed processes. Products include sugar streams, purified sugars, fermentation products (any of the disclosed biofuels or biochemicals), and lignin and lignin derivatives. Also, the invention includes a novel lignocellulosic intermediate material comprising, on a dry basis, about 0.1 wt %, 0.2 wt %, 0.3 wt %, 0.4 wt %, 0.5 wt %, 0.6 wt %, 0.7 wt %, 0.8 wt %, 0.9 wt %, 1 wt %, or more sucrose. The lignocellulosic intermediate material contains less than the sucrose content of typical fresh sugarcane (or sugar beets) and more than the sucrose content of typical crushed bagasse (or sugar beet pulp).

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for refining a sucrose-containing feedstock, said process comprising:
   (a) providing a feedstock containing lignocellulosic material and sucrose;
   (b) mechanically treating said feedstock to generate a sucrose-rich stream and sucrose-depleted lignocellulosic material, wherein said sucrose-depleted lignocellulosic material retains at least 1% of the initial sucrose contained in said feedstock;
   (c) extracting said sucrose-depleted lignocellulosic material with steam and/or hot water to produce cellulose-rich solids and an extract liquor containing hemicellulosic oligomers and extracted sucrose;
   (d) hydrolyzing said hemicellulosic oligomers into a hemicellulose sugar stream, wherein said hemicellulose sugar stream comprises said extracted sucrose or a hydrolyzed form thereof;
   (e) recovering or further processing said hemicellulose sugar stream;
   (f) recovering or further processing said sucrose-rich stream; and
   (g) combusting said cellulose-rich solids to produce steam and/or electricity.

2. The process of claim 1, wherein said feedstock is selected from the group consisting of sugarcane, energy cane, sugar beets, and energy beets.

3. The process of claim 2, wherein said feedstock is sugarcane and said lignocellulosic material contains sugarcane bagasse and optionally sugarcane straw.

4. The process of claim 1, wherein said extracted lignocellulosic material retains at least 2% of said initial sucrose contained in said feedstock.

5. The process of claim 4, wherein said extracted lignocellulosic material retains at least 5% of said initial sucrose contained in said feedstock.

6. The process of claim 1, wherein said extracted lignocellulosic material retains from about 1% to about 10% of said initial sucrose contained in said feedstock.

7. The process of claim 6, wherein said extracted lignocellulosic material retains from about 3% to about 6% of said initial sucrose contained in said feedstock.

8. The process of claim 1, wherein step (c) further includes introducing an extraction catalyst selected from an organic acid, an inorganic acid, or combinations thereof.

9. The process of claim 1, wherein step (d) employs an acid catalyst for said hydrolyzing said hemicellulosic oligomers.

10. The process of claim 1, wherein step (d) employs an enzyme catalyst for said hydrolyzing said hemicellulosic oligomers.

11. The process of claim 1, wherein at least a portion of said hemicellulose sugar stream is fermented to a fermentation product.

12. The process of claim 1, wherein at least a portion of said hemicellulose sugar stream is recovered as purified hemicellulose sugars.

13. The process of claim 1, wherein at least a portion of said sucrose-rich stream is fermented to ethanol or another fermentation product.

14. The process of claim 1, wherein at least a portion of said sucrose-rich stream is recovered as purified sucrose sugar.

15. A process for refining sugarcane, said process comprising:
   (a) providing a feedstock containing sugarcane;
   (b) mechanically treating said feedstock to generate a sucrose-rich stream and sucrose-depleted lignocellulosic material, wherein said sucrose-depleted lignocellulosic material retains from about 1% to about 10% of the initial sucrose contained in said sugarcane;
   (c) extracting said sucrose-depleted lignocellulosic material with steam and/or hot water to produce cellulose-rich solids and an extract liquor containing hemicellulosic oligomers and extracted sucrose;
   (d) hydrolyzing said hemicellulosic oligomers into a hemicellulose sugar stream, wherein said hemicellulose sugar stream comprises said extracted sucrose or a hydrolyzed form thereof;
   (e) recovering or further processing said hemicellulose sugar stream;
   (f) recovering or fermenting said sucrose-rich stream; and
   (g) combusting said cellulose-rich solids to produce steam and/or electricity.

16. A process for refining a sucrose-containing feedstock, said process comprising:
   (a) providing a feedstock containing lignocellulosic material and sucrose;
   (b) mechanically treating said feedstock to generate a sucrose-rich stream and sucrose-depleted lignocellulosic material, wherein said extracted lignocellulosic material retains at least 1% of the initial sucrose contained in said feedstock;
   (c) extracting said sucrose-depleted lignocellulosic material with steam and/or hot water to produce cellulose-rich solids and an extract liquor containing hemicellulosic oligomers and extracted sucrose;
   (d) hydrolyzing said hemicellulosic oligomers into a hemicellulose sugar stream, wherein said hemicellulose sugar stream comprises said extracted sucrose or a hydrolyzed form thereof;
   (e) recovering or further processing said hemicellulose sugar stream; and
   (f) recovering or further processing said sucrose-rich stream.

17. The process of claim 16, wherein said cellulose-rich solids are combusted to produce steam and/or electricity.

18. The process of claim 16, wherein said cellulose-rich solids are pelletized.

19. The process of claim 16, wherein said cellulose-rich solids are utilized as a pulp intermediate or pulp product.

20. The process of claim 16, wherein said cellulose-rich solids are hydrolyzed to produce glucose.

* * * * *